United States Patent [19]

Teng et al.

[11] Patent Number: 5,250,082

[45] Date of Patent: Oct. 5, 1993

[54] ENCAPSULATED STRUCTURE FOR PLANT INITIATE MATERIAL

[75] Inventors: Whei-Lan Teng; Yann-Jiun Liu; Chiao-Po Lin; Tai-Sen Soong, all of Taipei, Taiwan

[73] Assignee: Development Center for Biotechnology, Taipei, Taiwan

[21] Appl. No.: 946,095

[22] Filed: Sep. 17, 1992

Related U.S. Application Data

[63] Continuation-in-part of Ser. No. 678,057, Jan. 4, 1991, abandoned.

[51] Int. Cl.$^5$ .................. A01C 1/06; A01H 4/00
[52] U.S. Cl. ...................................................... 47/57.6
[58] Field of Search ............... 47/57.6, 58, DIG. 11; 424/456, 473, 424, 438, 469, 439, 420, 408, 456, 463, 451, 452, 405; 427/4; 604/890, 892; 435/240.22

[56] References Cited

U.S. PATENT DOCUMENTS

| | | | |
|---|---|---|---|
| 2,736,139 | 2/1956 | Wise | 47/58.01 |
| 4,220,153 | 9/1980 | Dresback | 424/438 |
| 4,309,996 | 1/1982 | Theeuwes | 424/424 |
| 4,769,027 | 9/1988 | Baker et al. | 424/493 |
| 4,769,945 | 9/1988 | Motoyama et al. | 47/57.6 |
| 4,781,714 | 11/1988 | Eckenhoff et al. | 424/424 |
| 5,010,685 | 4/1991 | Sakamoto et al. | 427/4 |
| 5,030,452 | 7/1991 | Curatolo | 424/451 |
| 5,120,548 | 6/1992 | McClelland et al. | 424/424 |

Primary Examiner—James R. Feyrer
Attorney, Agent, or Firm—Cushman Darby & Cushman

[57] ABSTRACT

Disclosed is an encapsulated structure for plant initiate material. Plant initiate material is encapsulated in a waterproof membrane coating or waterproof capsule, onto which water swellable polymeric material particles are partly embedded. This structure provides the encapsulated plant initate material with sufficient pressure resistance to endure rough handling, and allows the plant initiate material to gerninate without difficulty since during imbibition the water swellable particles would swell after absorbing water and thus break the waterproof memebrane coating or the waterproof capsule.

11 Claims, 1 Drawing Sheet

ENCAPSULATED STRUCTURE FOR PLANT INITIATE MATERIAL

This application is a continuation in part of U.S. patent application Ser. No. 07/678,057 filed on Jan. 4, 1991 and now abandoned.

BACKGROUND OF THE INVENTION

The present invention relates to an encapsulated structure for plant initiate material, and particularly to delivery and germination of plant initiate material.

There are numerous techniques or methods for plant initiate material encapsulation. One of the most popular types is to use alginate as encapsulation material (see U.S. Pat. No. 4,562,663). A disadvanage of this type is that the concentration of alginate has significant impact over the germination of encapsulated plant initiate material. For example, the pressure resistance of capsule made of 3% alginate is approximately 1.2 Kg, a pressure sufficient to inhibit the germination of encapsulated plant initiate material. Although when alginate concentration is decreased to 2%, germination of encapsulated plant initiate material would not be affected, the pressure resistance becomes only 0.8 Kg, thus the artificial seed is too soft for rough handling. Another disadvantage of using alginate as encapsulation material is that alginate capsule is very sticky and dries out rapidly when exposed in the air (Redenbaugh et al., 1987 HortSci. 22:803).

To prevent water loss of the capsule, a new technique was developed whereby a membrane was coated on the alginate capsule. The number of the membrane coating depends on the requirements of the encapsulation (see U.S. Pat. No. 4,715,143). Unfortunately, once the membrane coating(s) prevents the capsule from drying out quickly, germination of the encapsulated plant initiate material is also restricted (Redenbaugh et al., U.S. Pat. No. 4,175,143; Redenbaugh et al., 1987. HortSci. 22:803).

U.S. Pat. No. 4,769,945 discloses a delivery unit for plant tissue whereby the capsule is made of water soluble material but its interior is covered with water insoluble material. During imbibition, the capsule can be dissolved upon contacting with water, thus, whether the waterproof layer can be broken through depends totally on the force generated by the germinating plant initiate material. Consequently, the germination of the encapsulated plant initiate material depends entirely on the rigidity and thickness of the waterproof layer. The major disadvantage of these methods is that small embryos, such as those from seeds of Cruciserae, may have difficulty penetrating through the waterproof layer.

SUMMARY OF THE INVENTION

It is an object of the present invention to provide a technique for plant initiate material encapsulation whereby plant inate material is able to germinate with little difficulty.

It is another object of the present invention that the encapsulation is sufficient both to protect the encapsulated plant initiate material and to withstand rough handling during delivery.

In order to attain the above objects of the present invention, the encapsulated structure for plant initiate material of the present invention comprises: a waterprooof membrane coating; a hydro-gel encapsulated plant initiate material covered in the waterproof membrane coating, and water swellable polymeric material particles partly embedded in the waterproof membrane coating.

In case an artificial endosperm is used, the encapsulated structure of the present invention comprises: a capsule body made of waterproof material; water swellable polymeric material particles partly embedded in the capsule body; an artificial endosperm occupying a portion of the capsule body and forming an air chamber in the capsule body; and a plant initiate material placed on the artificial endosperm.

DETAILED DESCRIPTION OF THE INVENTION

Plant initiate material includes zygotic embryo, cell cluster, callus, plantlet, somatic embryo, etc. The present invention is particularly suitable for transportation of small somatic embryos from one place to another without hindering the germination of embryos.

The hydro-gel includes agar and alginate.

There are two essential requirements to the election of suitable material for the waterproof membrane coating and capsule body: (1) nontoxicity to plant initiate material, and (2) water insolubility. Some of the suitable materials are rosin, gum damma, gum mastic, wax, gum guaiac, silicone elastomer, polystyrene, ethyl cellulose, polyvinyl chloride, etc.

Materials that absorb water and swell during imbibition can be used for the water swellable particles in the present invention. Some examples are acrylate, copolymer acrylamide acrylate, methacrylamide, acrylnitrile, hydroxyalkyl acrylate hydrophilic polymer, etc.

The artificial endosperm can be nutrient agar media or soiless culture media with nutrient solution.

The capsule body can be in the shape of oval, tube, sphere, ellipse or cube.

According to the present invention, the plant initiate material is encapsulated in a waterproof membrane coating or in a waterproof capsule body, onto which water swellable particles are partly embedded. Under the structure, the encapsulated plant initiate material is provided with sufficient pressure resistance to endure rough handling. The structure also allows the plant initiate material to germinate without difficulty since during imbibition the water swellable particles would swell after absorbing water and thus break the waterproof membrane coating or capsule body.

BRIEF DESCRIPTION OF THE DRAWINGS

This invention is more specifically described by the following examples and illustrative examples with accompanying drawings, wherein:

As shown in FIG. 1. the encapsulated somatic embryo is spherical in shape. The encapsulated body 1 comprises a membrane coating 2, which is made of waterproof material, and water swellable particles 3, which are partly embedded in the membrane coating 2. A hydro-gel 5 encapsulated somatic embryo 4 is further encapsulated inside the encapsulated body 1.

Figure 2:
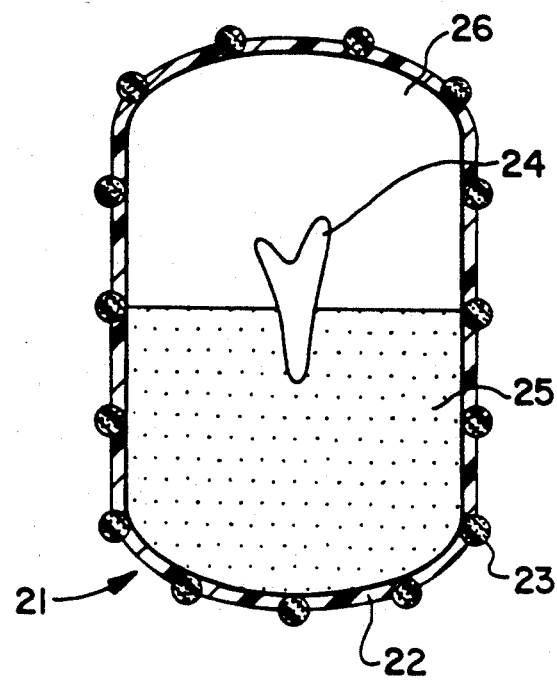
FIG. 2 is a sectional view of an encapsulated somatic embryo placed on an artificial endosperm of another embodiment of the present invention.

Another embodiment of the present invention is shown in FIG. 2, where the ellipsoidal body 21 comprises a capsule body 22, which is made of waterproof material, and water swellable particles 23, which are partly embedded in the capsule body 22. The somatic embryo 24 is placed onto the surface of an artificial endosperm 25 made of either nutrient agar medium or soiless culture medium with nutrient solution. Agar media contain carbohydrates for growth and development. Soiless culture media include, inter alia, perlite, vermiculite, resin, peatmoss and hydrophilic gels mixed with additional nutrient solutions. Furthermore, there is an air chamber 26 above the artificial endosperm 25 to allow respiration of somatic embryo 24.

EXAMPLE 1

Figure 1:
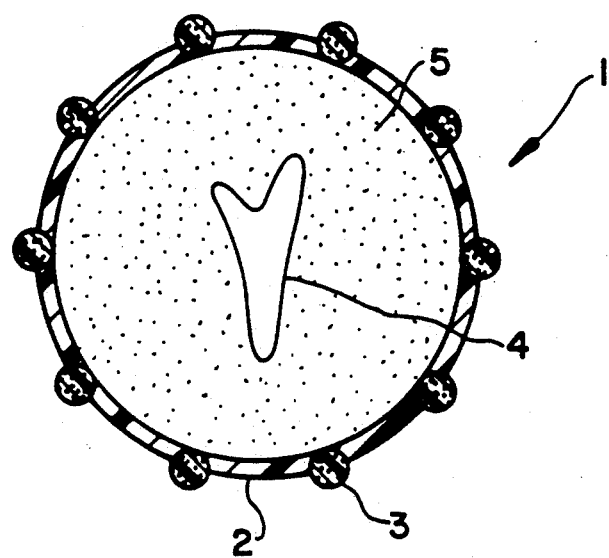
FIG. 1 is a sectional view of an alginate encapsulated somatic embryo of an embodiment according to the present invention.

The encapsulated stucture of Example 1 is shown in FIG. 1. The plant initiate material used was the somatic embryo of carrot. The somatic embryo was first encapsulated with 2% alginate, following the protocol in U.S. Pat. No. 4,562,663. Each of the following four materials was then individually used as waterproof membrane coating for second encapsulation: the alcohol solution of rosin, gum damma, gum guaiac and wax of 60° C. Both acrylate and copolymer acrylamide acrylate were used individually as water swellable material.

The process of the second encapsulation involves dipping the alginate encapsulated somatic embryo into the solution of water insoluble material. The embryo was then covered with water swellable particles before its waterproof membrane coating solidifies. The water swellable particles were then slightly pressed into the waterproof membrane coating so that they were partly embedded in it.

For comparison, two sets of controls were prepared: (i) a somatic embryo of carrot encapsulated with 2% alginate, following the protocol in U.S. Pat. No. 4,562,663, and (ii) an encapsulated somatic embryo as in control (i) with a further coating of a waterproof material, following the protocol in U.S. Pat. No. 4,715,143.

All the encapsulated somatic embryos including the present invention and two sets of controls were placed on both solid MS medium (Murashige and Skoog, 1962) and sterilized soiless culture media for germination test. The germination rate of the present invention was the same as that of the control (i) but faster than that of the control (ii).

EXAMPLE 2

The structure of Example 2 is shown in FIG. 1. The zygotic embryos of Chinese cabbage, rape and caraway were encapsulated individually, as decribed in Example 1. The outcome of this Example was essentially the same as that of Example 1.

In the case of these examples, water swellable particles broke the waterproof coat without difficulty during imbibition. Therefore, the present invention, because of its encapsulated structure, is able to enhance water preservation of the capsule. The present invention also allows a structure with sufficient stiffness for rough handling without inhibiting the germination of the encapsulated embryo.

Although the present invention has been described in some detail through illustrations and examples, the scope of the present invention shall not be limited to the contexts of the examples, which were used purely for illustration purposes, and shall cover any improvements based on the principle ideas of the present invention.

What is claimed is:

1. An encapsulated structure of plant initiate material comprising:
    a non-toxic waterproof membrane coating;
    a hydro-gel encapsulated plant initiate material covered in said waterproof membrane coating; and
    water swellable polymeric material particles partly embedded in said waterproof membrane coating such that said particles do not penetrate through the membrane coating.

2. An encapsulated structure as claimed in claim 1, wherein said hydro-gel material is selected from the group consisting of agar and alginate.

3. An encapsulated structure as claimed in claim 1, wherein said plant initiate material is selected from the group cosisting of zygotic embryo, cell cluster, callus, plantlet, and somatic embryo.

4. An encapsulated structure as claimed in claim 1, wherein said non-toxic waterproof membrane coating is made of water insoluble material selected from the group consisting of rosin, gum damma, gum mastic, wax, gum guaiac, silicone elastomer, ethyl cellulose, polystyrene and polyvinyl chloride.

5. An encapsulated structure as claimed in claim 1, wherein said water swellable polymeric material particles is selected from the group consisting of acrylate, copolymer acrylamide acrylate, methacrylamide, acrylnitrile and hydroxalkyl acrylate hydrophilic polymer.

6. An encapsulated structure of plant initiate material comprising:
    a capsule body made of non-toxic waterproof materials;
    water swellable polymeric material particles partly embedded in said capsule body such that said particles do not penetrate through the capsule body;
    an artificial endosperm occupying a portion in said capsule body and forming an air chamber in said capsule body; and
    a plant initiate material placed on said artificial endosperm.

7. An encapsulated structure as claimed in claim 6 wherein said non-toxic waterproof capsule is made of water insoluble material selected from the group consisting of rosin, gum damma, gum mastic, wax, gum guaiac, silicone elastomer, ethyl cellulose, polystyrene and polyvinyl chloride.

8. An encapsulated structure as claimed in claim 6, wherein said water swellable polymeric material particles is selected from the group consisting of acrylate, copolymer acrylamide acrylate, methacrylamide, acrylonitrile and hyfroxalkyl acrylate hydrophilic polymer.

9. An encapsulated structure as claimed in claim 6, wherein said plant initate material is selected from the group cosisting of zygotic embryo, cell cluster, callus, plantlet, and somatic embryo.

10. An encapsulated structure as claimed in claim 6, wherein said artificial endosperm is made from media selected from the group consisting of nutrient agar media and soil-less culture media with nutrient solution.

11. An encapsulated structure as claimed in claim 6, wherein the capsule body is in the shape of oval, tube, sphere, ellipse, or cube.

* * * * *